(12) United States Patent
Kato et al.

(10) Patent No.: US 6,482,650 B1
(45) Date of Patent: *Nov. 19, 2002

(54) METHOD FOR DETECTING DETERIORATION OF CATALYST

(75) Inventors: Nobuhide Kato, Aichi-prefecture (JP); Nobukazu Ikoma, Nagoya (JP); Satoshi Nishikawa, Nagoya (JP); Takeya Miyashita, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,058

(22) Filed: Feb. 25, 1999

Related U.S. Application Data

(62) Division of application No. 08/667,794, filed on Jun. 21, 1996, now Pat. No. 5,922,287.

(30) Foreign Application Priority Data

Jun. 26, 1995 (JP) .............................. 7-159683

(51) Int. Cl.$^7$ .............................................. G01N 31/10
(52) U.S. Cl. ...................... 436/37; 436/139; 436/143; 436/152; 436/159
(58) Field of Search .................. 436/37, 139, 143, 436/147, 155, 159, 160, 149, 150, 151, 152; 422/94–97, 78, 80, 82.01

(56) References Cited

U.S. PATENT DOCUMENTS

| 3,906,721 | A | * | 9/1975 | Mitcheli et al. |
| 4,164,539 | A | * | 8/1979 | Johnston |
| 4,242,302 | A | * | 12/1980 | Kitamura et al. |
| 5,265,417 | A | | 11/1993 | Visser et al. ................ 60/274 |
| 5,549,871 | A | | 8/1996 | Kocache et al. ............. 422/95 |
| 5,922,287 | A | * | 7/1999 | Kato et al. |

FOREIGN PATENT DOCUMENTS

| JP | 62-61919 U | | 4/1987 |
| JP | 4-279831 A | | 10/1992 |
| WO | 95/10770 | * | 4/1995 |

* cited by examiner

Primary Examiner—Jan Ludlow
(74) Attorney, Agent, or Firm—Kubovcik & Kubovcik

(57) ABSTRACT

One of a pair of temperature sensor sections in a combustible gas sensor is covered with porous oxidizing catalytic layers (23, 24) for oxidizing a combustible gas, and the other is not covered with the oxidizing catalyst layers. The temperature sensor sections each have temperature sensitive portions (13, 14) made of a dense ceramic material, resistors (21, 22) buried therein and having a positive resistance temperature coefficient, current leads (31, 32, 41, 42) and voltage leads (33, 34, 43, 44). A method for detecting the deterioration of a catalyst which intends to eliminate the combustible gas, by the use of this combustible gas sensor is further disclosed. When a difference between temperatures of the pair of resistors or a difference between powers fed to the pair of resistors is in excess of a predetermined value, it is judged that the catalyst has been deteriorated.

4 Claims, 10 Drawing Sheets

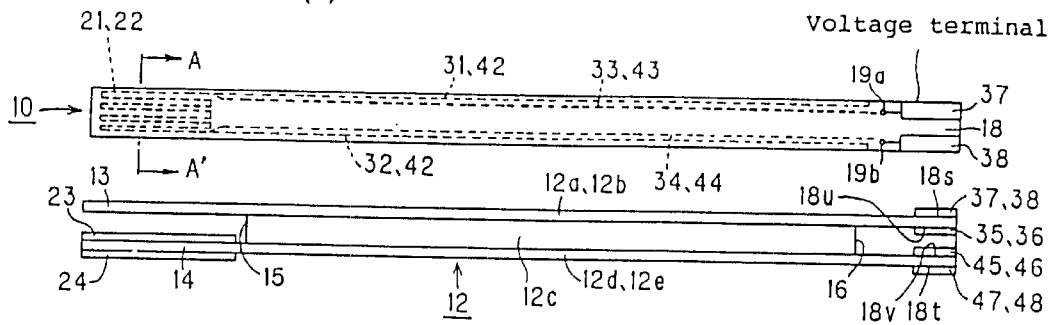
FIG. 1(a)
FIG. 1(b)
FIG. 1(c)
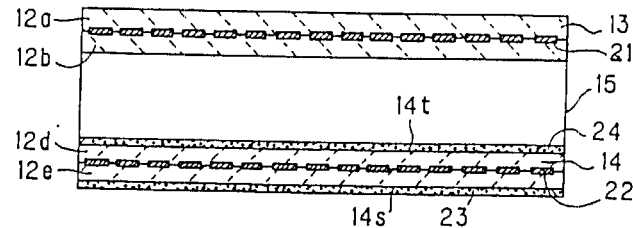
FIG. 2
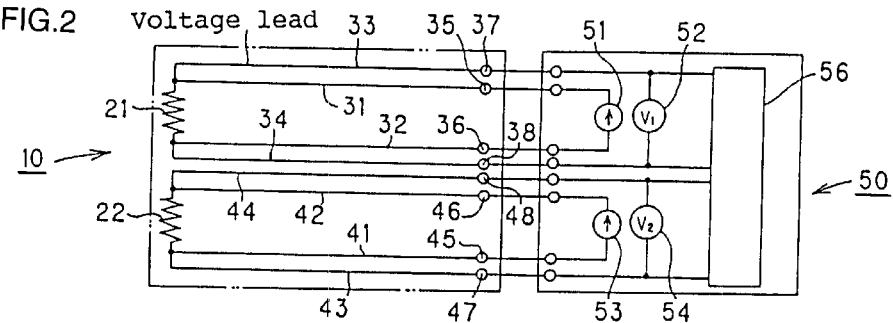
FIG. 3
$R(\Omega)=30.0(1+3908\cdot10^{-6}t-0.576\cdot10^{-6}t^2)$
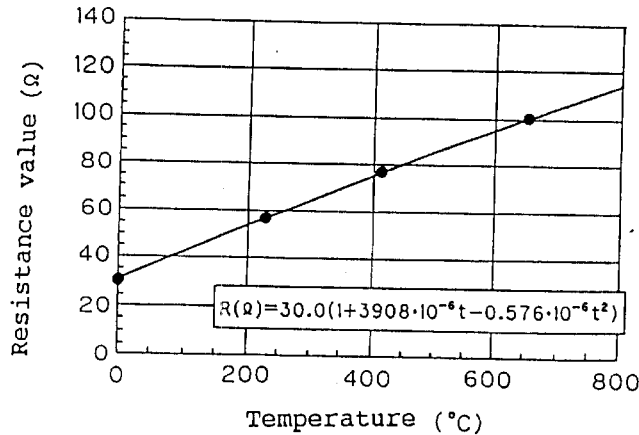

METHOD FOR DETECTING DETERIORATION OF CATALYST

This application is a division of application Ser. No. 08/667,794, filed Jun. 21, 1996 now U.S. Pat. No. 5,922,287.

BACKGROUND OF THE INVENTION (i) Field of the Invention

The present invention relates to a combustible gas sensor for detecting a combustible gas contained in a gas to be measured. The present invention also relates to a method for detecting the deterioration of a catalyst for cleaning the exhaust gas of an automobile.

(ii) Description of the Related Art

A combustible gas sensor intends to detect a combustible gas contained in a gas to be measured, such as a gas generated at combustion or an exhaust gas, and it has been required to quantitatively determine the concentration of the combustible gas by the sensor. The exhaust gas is exhausted from, for example, an internal combustion engine, an external combustion engine or a combustion furnace which utilizes heavy oil, gas oil, gasoline, a natural gas or the like as a fuel.

In the combustible gas sensor, the so-called contact combustion type is employed, and in this type, the combustible gas is burned with the aid of a platinum catalyst and a temperature raised by the combustion heat is then measured. In a conventional contact combustion type combustible gas sensor, an oxidation catalyst of a noble metal such as Pt, Pd or Rh is supported on beads formed by sintering alumina in a porous state on a platinum coil. The platinum coil is heated by an external heater up to about 300° C. and then brought into contact with the gas to be measured, so that combustion occurs to raise the temperature of the platinum coil. The thus raised temperature is then detected as a change of the electric resistance of the platinum wire buried in the beads by means of a bridge circuit.

The conventional combustible gas sensor, however, is constituted so that the combustible gas may come in contact with the platinum resistor, and therefore when the sensor is used at a temperature as high as 900° C. the resistance value of the platinum resistor changes inconveniently. Thus, the conventional combustible gas sensor has a drawback that its use at a high temperature is impossible. In addition, when the temperature of the gas to be measured changes remarkably, for instance, when it changes from room temperature to about 900° C. there is no way to accurately measure the temperature rise attributable to the heat generation of the combustible gas contained therein.

On the other hand, various combustible gas sensors using oxide semiconductors have also been investigated. However, the oxide semiconductor type combustible gas sensor has a disadvantage that its performance is vitally affected by oxygen, humidity or the like, and another disadvantage that the resistance value of the semiconductor changes at a high temperature.

Heretofore, there has been researched a method for detecting the deterioration of a catalyst such as an exhaust gas cleaning catalyst which intends to eliminate the combustible gas. For instance, Japanese Utility Model Application Laid-open No. 61919/1987 has suggested a method for detecting the deterioration of a catalyst which comprises arranging temperature sensors on the upstream side and on the downstream side of the catalyst, respectively, and then comparing a temperature of the exhaust gas on the upstream side with that of the exhaust gas on the downstream side. In this method, the deterioration of the catalyst is required to be judged after an automobile has run at a constant speed of 40 to 60 km/hr for several minutes. This constant running is necessary to thermally stabilize an exhaust system, because the catalyst has a large heat capacity. Thus, in order to improve the detection accuracy of the catalyst deterioration, the automobile is required to run at the constant speed for a further long time.

However, under actual running conditions of the automobile where acceleration and deceleration are repeated, the above-mentioned requirement of the running at the constant speed can hardly be met, and therefore it is difficult to detect the deterioration of the catalyst with a high precision. Furthermore, in this method, a sufficient temperature difference cannot be obtained unless the temperature sensors are inserted into an exhaust tube so that they may be close to the central axis of the exhaust tube, and hence this method has a drawback that the pressure of the exhaust gas is increased and the output power of the engine is consequently reduced. In addition, the two temperature sensors are required, which makes the system complicated, with the result that cost increases inconveniently.

When the combustible gas sensor is used in the exhaust system of the automobile, the output of the sensor element is connected to an electronic device other than the sensor element, a central processing unit or the like, and the temperature or the like is detected by the electronic device, the central processing unit or the like. Here, a resistance value R of a resistor having a positive resistance temperature coefficient is represented by $R=R_0(1+\alpha t-\beta t^2)$ wherein t is a temperature, and $R_0$ is a resistance value of the resistor at 0° C. but it is not limited to the resistance value at 0° C. and it may be the definite resistance value of the resistor at a certain temperature.

Accordingly, in order that the electronic device, the central processing unit or the like measures the temperature or the like, it is necessary that the resistance value at the certain temperature of the resistor in the specific sensor element connected to the electronic device or the like should be previously input to the electronic device or the like. Furthermore, when the sensor elements are attached to the automobiles on such a mass production line as in an assembly plant of the automobiles, the resistance value of the resistor in each sensor element is required to be promptly put to the electronic device or the like. For example, it is impractical that the resistance value of the resistor is input to the computer of each automobile by way of a keyboard.

However, in the process of manufacturing the sensor elements, the resistance value of the resistor may inevitably scatter to some extent. For example, the resistor can often be formed by printing its pattern on the surface of a ceramic green sheet and then baking the green sheet having the resistor pattern. The resistance value of the thus formed resistors typically has a deviation of ±10%.

Japanese Patent Application Laid-open No. 279831/1992 has described a technique of trimming the resistor by means of laser irradiation in order to minimize the deviation in the resistance values of the resistor. However, when the resistor is trimmed by the laser irradiation, the temperature of the resistor rises. Since the resistor has a large resistance temperature coefficient, it is difficult to heighten the precision of the resistance value of the resistor, so that the resistance value of each sensor element largely scatters sometimes.

SUMMARY OF THE INVENTION

An object of the present invention is to provide a combustible gas sensor which is excellent in durability at a high temperature and which can hence measure a gas to be measured even if its temperature noticeably fluctuates.

Another object of the present invention is to provide a method for using the combustible gas sensor, particularly a method for measuring the concentration of a combustible gas.

Still another object of the present invention is to provide a method for detecting, with a high precision, the deterioration of a catalyst which intends to eliminate the combustible gas, even if the temperature of the gas to be measured fluctuates.

According to the first aspect of the invention, there is provided a combustible gas sensor which comprises a base member having a first temperature sensitive portion of a dense ceramic material and a second temperature sensitive portion of a dense ceramic material, a first temperature sensor section and a second temperature sensor section; the first temperature sensor section being provided with the first temperature sensitive portion, a first resistor buried in the first temperature sensitive portion and having a positive resistance temperature coefficient, a first pair of current leads for feeding current to the first resistor and a first pair of voltage leads for detecting the voltage of the first resistor; the second temperature sensor section being provided with the second temperature sensitive portion, a second resistor buried in the second temperature sensitive portion and having a positive resistance temperature coefficient, a second pair of current leads for feeding current to the second resistor, a second pair of voltage leads for detecting the voltage of the second resistor and a porous oxidation catalyst layer which covers at least a part of the surface of the second temperature sensitive portion and which catalyzes the oxidation of a combustible gas.

In the present invention, it is preferred that the first resistor is connected to a first pair of current terminals and a first pair of voltage terminals by way of the first pair of current leads and the first pair of voltage leads, and the second resistor is connected to a second pair of current terminals and a second pair of voltage terminals by way of the second pair of current leads and the second pair of voltage leads.

It is preferred that the first and second temperature sensitive portions have substantially identical shapes and are made of substantially identical materials, and the first and second resistors have substantially identical shapes and are made of substantially identical materials.

Furthermore, a space may be formed between the first temperature sensitive portion and the second temperature sensitive portion, or the space between the first temperature sensitive portion and the second temperature sensitive portion may be filled with the base member.

It is preferred that the first temperature sensitive portion has a first dense ceramic layer covering the first resistor; the second temperature sensitive portion has a second dense ceramic layer covering the second resistor; and the oxidation catalyst layer covers the second dense ceramic layer.

In addition, the base member including the first temperature sensitive portion and the second temperature sensitive portion preferably contains 99% or more of alumina.

Preferably, the oxidation catalyst layer has a cermet layer covering at least a part of the surface of the second temperature sensitive portion; the cermet layer has a skeletal structure containing a ceramic material and a metal which functions as an oxidation catalyst; the skeletal structure is porous; and the particles of the metal are supported on the inner surface of the skeletal structure.

Preferably, at least a part of the surface of the first temperature sensitive portion is covered with a first catalyst layer; at least a part of the surface of the second temperature sensitive portion or the oxidation catalyst layer is covered with a second catalyst layer; and both the first catalyst layer and the second catalyst layer contain a catalyst for oxidizing carbon monoxide.

Preferably, the first temperature sensor section further has a first potentiometric resistor connected in parallel to the first resistor; the resistance of the first potentiometric resistor is regulated by trimming so that an output voltage generated at the feed of a predetermined current to the first resistor may be a predetermined value; the second temperature sensor section further has a second potentiometric resistor connected in parallel to the second resistor; and the resistance of the second potentiometric resistor is regulated by trimming so that an output voltage generated at the feed of a predetermined current to the second resistor may be a predetermined value.

Preferably, the first temperature sensor section further has a first serial resistor connected in series to the first resistor by way of the first pair of voltage leads; the resistance of the first serial resistor is regulated by trimming so that the total of the resistances of the first resistor, the first serial resistor and the first pair of voltage leads may have a certain relation to the resistance of the first resistor; the second temperature sensor section further has a second serial resistor connected in series to the second resistor by way of the second pair of voltage leads; and the resistance of the second serial resistor is regulated by trimming so that the total of the resistances of the second resistor, the second serial resistor and the second pair of voltage leads may have a certain relation to the resistance of the second resistor.

Preferably, the resistance of the first serial resistor is regulated by trimming so that the total of the resistances of the first resistor, the first serial resistor and the first pair of voltage leads may be proportional to the resistance of the first resistor; and the resistance of the second serial resistor is regulated by trimming so that the total of the resistances of the second resistor, the second serial resistor and the second pair of voltage leads may be proportional to the resistance of the second resistor.

The combustible gas sensor of the present invention preferably has a heating/control means for heating and controlling the first resistor or the second resistor to a predetermined temperature. This heating/control means may have a variable power source for applying current or voltage to the first resistor or the second resistor, and the variable power source may regulate the current or the voltage so as to control the first resistor or the second resistor to a predetermined temperature in accordance with the resistance of the first resistor or the second resistor. Alternatively, the heating/control means may have a heater for regulating its output so as to control the first resistor or the second resistor to a predetermined temperature in accordance with the resistance of the first resistor or the second resistor.

According to a second aspect of the present invention, there is provided a method of measuring the concentration of a combustible gas by the use of the above-mentioned combustible gas sensor which comprises a step of applying a current $I_1$ to a first resistor to determine a voltage $V_1$ of the first resistor, a step of applying a current $I_2$ to the second resistor to determine a voltage $V_2$ of the second resistor, and a step of determining a difference between temperatures of the first resistor and the second resistor or a difference between electric power fed to the first resistor and the second resistor on the basis of the current $I_1$, the current $I_2$, the voltage $V_1$ and the voltage $V_2$.

In the present invention, it is preferred that the current $I_1$ is so weak as not to substantially raise the temperature of the first resistor, and the current $I_2$ is so weak as not to substantially raise the temperature of the second resistor.

Furthermore, according to a method for measuring the concentration of a combustible gas by the use of a combustible gas sensor having a heating/control means for heating and controlling the first resistor or the second resistor to a predetermined temperature, the temperature or the resistance of the second resistor may be determined by heating/controlling the first resistor to a predetermined temperature. Alternatively, a difference between electric powers fed to the first resistor and the second resistor may be determined by heating/controlling the first resistor and the second resistor to a predetermined temperature.

According to a third aspect of the present invention, there is provided a method for detecting the deterioration of a catalyst which intends to eliminate a combustible gas by the use of the above-mentioned combustible gas sensor, said method comprising the step of measuring the concentration of the combustible gas contained in a gas to be measured which is discharged through the catalyst, by the combustible gas sensor attached on the downstream side of the catalyst.

In the present invention, output signals of the combustible gas sensor may be accumulated for a predetermined period of time. Alternatively, there may be calculated a product of the output signal of the combustible gas sensor and the flow rate of the gas to be measured. In the case of the latter, the products are preferably accumulated for a predetermined period of time.

According to a fourth aspect of the invention, there is provided a sensor element which comprises a base member having a first temperature sensitive portion of a dense ceramic material and a second temperature sensitive portion of a dense ceramic material, a first temperature sensor section and a second temperature sensor section; the first temperature sensor section being provided with the first temperature sensitive portion, a first resistor buried in the first temperature sensitive portion and having a positive resistance temperature coefficient, a first pair of current leads for feeding current to the first resistor and a first pair of voltage leads for detecting the voltage of the first resistor; the second temperature sensor section being provided with a second temperature sensitive portion, a second resistor buried in the second temperature sensitive portion and having a positive resistance temperature coefficient, a second pair of current leads for feeding current to the second resistor and a second pair of voltage leads for detecting the voltage of the second resistor.

BRIEF DESCRIPTION OF THE DRAWINGS

FIG. 1A is a schematic front view of one embodiment of a combustible gas sensor according to the invention.

FIG. 1B is a schematic side view of the embodiment of FIG. 1A.

FIG. 1C is a schematic sectional view taken along the line A-A' in FIG. 1A.

FIG. 2 shows an electric circuit diagram of the combustible gas sensor shown in FIGS. 1A to 1C and an electric circuit diagram of an arithmetic device.

FIG. 3 is a graph showing the relation between the resistance and the temperature of a cermet.

DETAILED DESCRIPTION OF THE PREFERRED EMBODIMENTS

Figure 4:
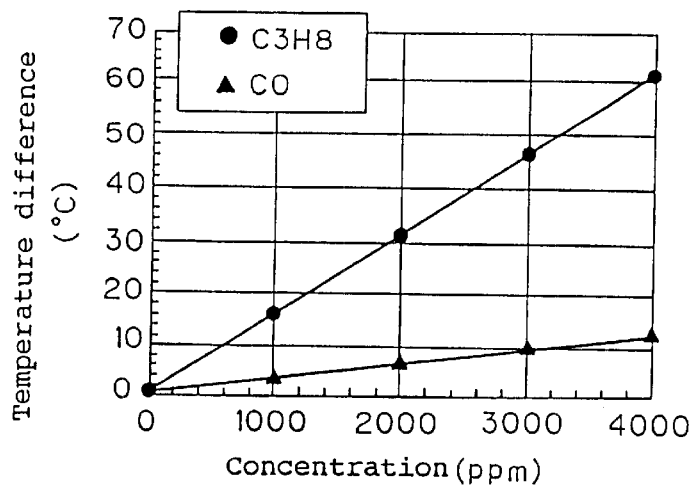
FIG. 4 is a graph showing the relation between a temperature difference between resistors 21 and 22 and the concentration of a combustible gas.

A combustible gas sensor according to the invention has a pair of temperature sensor sections. One of the temperature sensor sections is covered with an oxidation catalyst layer for oxidizing a combustible gas. On the contrary, the other temperature sensor section is not covered with the oxidation catalyst layer. When the combustible gas sensor is used, in the one temperature sensor section, the combustible gas contained in the gas to be measured is burned with the aid of the oxidation catalyst layer to raise the temperature of the temperature sensitive portion in the temperature sensor section. On the contrary, at the other temperature sensor section, any temperature does not rise, because this temperature sensor section is not covered with the oxidation catalyst layer. Thus, the concentration of the combustible gas can be determined by detecting a temperature difference between the temperature sensitive portions of the pair of temperature sensor sections. Alternatively, the concentration of the combustible gas can be determined by heating and controlling the two resistors to the same temperature and then calculating a difference between electric powers fed to the respective resistors.

In the present invention, all the resistors are buried in the respective temperature sensitive portions made of a dense ceramic material in order not to be exposed to the gas to be measured. Thus, even if the sensor is used at a high temperature, or in an oxidizing atmosphere or a reducing atmosphere, the resistors are hardly deteriorated owing to oxidization or the like. In consequence, the change of resistance values with time can be inhibited, and therefore even under such conditions, the sensor can be used.

Additionally, in the present invention, the temperature change of the gas to be measured can be compensated by using the pair of temperature sensor sections, and hence a temperature rise due to heat generation of the combustible gas can be accurately determined, even if the temperature of the gas to be measured fluctuates noticeably, for example, from room temperature to about 900° C.

The oxidation catalyst layer is porous into which the gas to be measured can be allowed to penetrate. This porous state permits the increase in the area of interfaces between a metal of the like which functions as a catalyst for oxidizing the combustible gas and the gas to be measured.

In the present invention, the pair of temperature sensor sections preferably have identical configurations as much as possible except the oxidation catalyst layer. For example, the shape, the material, the heat capacity and the like of the temperature sensitive portions and the resistors in both the temperature sensor sections are preferably identical as much as possible, whereby responsibility, 0-point calibration and the like can be improved.

When the temperature sensitive portions are both covered with the catalyst layers containing the catalyst for oxidizing carbon monoxide, respectively, sensitivity to hydrocarbons of components present in the combustible gas in the gas to be measured increases.

When the pair of temperature sensor sections both have potentiometric resistors connected in parallel to the resistors, respectively, the resistance of the potentiometric resistor can be regulated by trimming so that an output voltage generated at the feed of a predetermined current to the resistors may be a predetermined value. Therefore, the fluctuation of the output voltage of the temperature sensor section can be minimized. The combustible gas sensor, when used, is connected to an electronic device, a central processing unit and the like, but when the output voltage of the sensor element is a certain value, this output voltage can be input at one time to the electronic device and the like. Alternatively, the electronic device and the like can be regulated at one time to conditions where the output voltage of the sensor element corresponds to a specific value.

When the pair of temperature sensor sections both have serial resistors connected in series to the resistors by way of the voltage leads, respectively, the resistance of the serial resistors is regulated by trimming so that the total of the resistances of the resistor, the serial resistor and the pair of voltage leads may have a certain relation to the resistance of the resistor. For example, when the resistance of the resistor is 10 ohms, the resistance of the serial resistor is regulated so that the total resistance may be 10 kilo-ohms which is 1000 times as much as the above-mentioned resistance. Then, when the combustible gas sensor is used, the electronic device, the central processing unit and the like can detect the total resistance in the temperature sensor section, and the resistance of the resistor can be then calculated on the basis of the certain relation. For example, when it is detected that the total resistance of the resistor elements is 10 kilo-ohms, the resistance of the resistor is determined to be 10 ohms. With regard to this certain relation, the total of the resistances of the resistor, the serial resistor and the voltage leads is preferably proportional to the resistance of the resistor. In consequence, the resistance of the resistor in the temperature sensor section can be accurately and quickly input to another electronic device, the central processing unit and the like.

When the combustible gas sensor has the potentiometric resistor or the serial resistor and when the resistor does not heat itself, the concentration of the combustible gas can be measured by outputting the resistance of the resistor or an electric power fed to the resistor.

When the resistance of the resistor is output under conditions that the combustible gas sensor has the potentiometric resistor or the serial resistor and the resistor heats itself, the concentration of the combustible gas cannot be accurately measured in principle in the case of using the potentiometric resistor. On the other hand, in the case of using the serial resistor, the concentration of the combustible gas can be accurately measured. However, even if the potentiometric resistor is used, the concentration of the combustible gas can be accurately measured, provided that in the pair of temperature sensor sections, the shape, the material, the heat capacity, the heat release conditions and the like of the temperature sensitive portions are identical and the shape, the material and the heat capacity of the resistors are identical.

Furthermore, when the electric power fed to the resistor is output under conditions that the combustible gas sensor has the potentiometric resistor or the serial resistor and the resistor heats itself, the concentration of the combustible gas can be accurately measured in either of the case of using the potentiometric resistor and the case of using the serial resistor.

In a method for detecting the deterioration of a catalyst according to the present invention, a temperature difference between the temperature sensitive portions of the pair of temperature sensor sections, i.e., a temperature difference is measured, and if the temperature difference exceeds a predetermined value, it is judged that the catalyst is deteriorated. Alternatively, the resistors in the pair of temperature sensor sections are heated and controlled to the same temperature, and a difference between electric powers fed to the respective resistors, i.e., a power difference is measured. If the power difference exceeds a predetermined value, it is judged that the catalyst is deteriorated.

The sensor element according to the invention is useful as a precursor of the combustible gas sensor or the like, and it can be widely used in a temperature sensor, a heat type flow meter or the like in which the compensation of the temperature of the gas to be measured is required.

The preferred embodiments of the present invention are hereinbelow described in more detail with reference to the drawings.

FIGS. 1A to 1C show one embodiment of a combustible gas sensor according to the present invention. FIG. 1A is a front view, FIG. 1B is a side view, and FIG. 1C is a sectional view taken along the line A–A' in FIG. 1A.

A ceramic base member 12 has a pair of temperature sensitive portions 13, 14 for sensing the temperature of the gas to be measured, and a space 15 is formed between the temperature sensitive portions 13, 14. The temperature sensitive members 13, 14 are made of a dense ceramic material so that a gas such as an exhaust gas may not penetrate thereinto. Furthermore, the temperature sensitive portions 13, 14 are preferably arranged at an end portion of the ceramic base member 12, and they preferably have an identical shape and they are made of the same material.

Resistors 21 for measuring a temperature are buried in the temperature sensitive portion 13 so as not to come in contact with the gas to be measured. Likewise, other resistors 22 for measuring a temperature are buried in the temperature sensitive portion 14 so as not to come in contact with the gas to be measured. The resistors 21, 22 contain a metal having a positive resistance temperature coefficient, and this metal can measure the temperature by the utilization of characteristics by which its resistance value changes in accordance with a temperature change.

It is preferred that the resistors 21, 22 are made of the same material and have the substantially same shape. In FIG. 1A, each group of the resistors 21, 22 has one continuous line form, and two or more substantially parallel straight lines of the resistors 21, 22 are connected at their ends by a U-shaped connector. The temperature sensitive portions 13, 14 preferably have a thin planar form, and the resistors 21, 22 are preferably arranged in parallel with the planar surfaces of the sections 13, 14. In the present invention, however, the shape of the resistors 21, 22 is not restrictive.

A pair of oppositely disposed surfaces 14s and 14t of the temperature sensitive portion 14 are covered with oxidation catalyst layers 23, 24, which are porous so that the gas to be measured can penetrate thereinto. The oxidation catalyst layers contain an oxidation catalyst such as platinum in order to promote the combustion of a combustible gas. The oxidation catalyst layers preferably contain a cermet of the oxidation catalyst, which is the metal, and a ceramic material, for example, the cermet comprising Pt and $Al_2O_3$. In FIG. 1, each of the oxidation catalyst layers 23, 24 has a single layer structure. In the present invention, however, the structure of the oxidation catalyst is not limited to the single layer structure.

When the combustible gas is burned with the aid of the oxidation catalyst layers 23, 24, the temperature of the resistors 22 in the temperature sensitive portion 14 rises. On the contrary, the resistors 21 in the temperature sensitive portion 13 do not bring about the temperature rise, because the temperature sensitive portion 13 containing the resistors 21 is not covered with the oxidation catalyst layer. Thus, the combustible gas can be detected on the basis of a temperature difference between the resistors 21 and 22.

In this connection, the combustion heat can be transmitted from the oxidation catalyst layer 24 to the resistor 21, but the heat transmission can be minimized by the space 15.

Each of the resistors 21, 22 has a four terminal configuration. The resistor 21 is connected to a pair of current leads 31, 32, which are then connected to current terminals 35, 36. Meanwhile, the resistor 21 is connected to a pair of voltage leads 33, 34, which are then connected to voltage terminals 37, 38. The resistor 22 is connected to a pair of current leads 41, 42, which are then connected to current terminals 45, 46. Furthermore, the resistor 22 is connected to a pair of voltage leads 43, 44, which are then connected to voltage terminals 47, 48.

At an end portion 18 of the ceramic base member 12, a space 16 is formed. A pair of through holes 19a, 19b are formed at the end portion 18 of the ceramic base member 12, and these through holes 19a, 19b are communicated with the space 16. The pair of voltage leads 33, 34 are connected to the voltage terminals 37, 38 by way of the through holes 19a, 19b.

The current terminals 35, 36 cover an inner surface 18u of the end portion 18. The voltage terminals 37, 38 cover an outer surface 18s of the end portion 18. The current terminals 45, 46 cover the inner surface 18v of the end portion 18. The voltage terminals 47, 48 cover the outer surface 18t of the end portion 18.

FIG. 2 shows an electric circuit diagram of the combustible gas sensor shown in FIGS. 1A to 1C and an electric circuit diagram of an arithmetic device.

The combustible gas sensor 10 of the present invention can be used together with an arithmetic device 50. This arithmetic device 50 comprises constant current sources 51, 53, voltmeters 52, 54 and an arithmetic circuit 56. This arithmetic device is, for example, a computer or an interface in an automobile.

A current is fed to the current leads 31, 32 from the constant current source 51, and the voltage across the resistor 21 is measured by way of the voltage leads 33, 34 by the voltmeter 52. Likewise, a current is fed to the current leads 41, 42 from the constant current source 51, and the voltage of the resistor 22 is measured by way of the voltage leads 43, 44 by the voltmeter 54.

The sensor element 10 is prepared by, for example, laminating five green sheets 12a, 12b, 12c, 12d, 12e in this order, and then baking them. On one surface of the green sheet 12a, the voltage terminals 37, 38 are formed by printing. On one surface of the green sheet 12b, the resistor 21, the current leads 31, 32 and the voltage leads 33, 34 are formed by printing, and on the other surface thereof, the current terminals 35, 36 are formed by printing. The green sheet 12c is shorter than the other green sheets. On the surface of the green sheet 12d, the oxidation catalyst layer 23 is formed by printing. On one surface of the green sheet 12e, there are formed the resistor 22, the current leads 41, 42 and the voltage lead 43, 44 by printing, and on the other surface thereof, the oxidation catalyst layer 22 and the voltage terminals 47, 48 are formed by printing. Next, these green sheets are laminated, and the green sheets 12a, 12b, 12c, 12d, 12e, the resistors 21, 22 and the oxidation catalyst layers 23, 24 are then simultaneously baked.

Alternatively, the green sheet 12c may be replaced by a spacer 12c. Thus, a baked laminate of the spacer 12c and the green sheets 12a, 12b may be bonded to a baked laminate of the green sheet 12d and the green sheet 12e by cement or glass.

After the baking, it is preferred that the oxidation catalyst layer is subjected to a reduction treatment and noble metal particles which function as an oxidation catalyst are then supported on the oxidation catalyst layer in order to enhance its oxidation catalyst performance. This operation can be accomplished by impregnating the oxidation catalyst layer with a chloroplatinic acid solution, and then heating the same at about 70° C.

As the oxidation catalyst layer, a cermet layer having a skeletal structure containing a ceramic material and a metal which functions as an oxidation catalyst can be formed by printing and then baking a cermet. Preferably, the metal particles functional as the oxidation catalyst are supported on the inner surface of the skeletal structure of the cermet layer which is porous.

Now, reference will be made to the operation of the combustible gas sensor 10 and the method for measuring the concentration of the combustible gas by the use of the combustible gas sensor 10.

The surfaces of the temperature sensitive portion 13 of the ceramic base member 12 are not covered with any oxidation catalyst layer. Therefore, the resistor 21 shows a resistance value corresponding to the temperature of the gas to be measured such as an exhaust gas.

On the other hand, the surfaces of the temperature sensitive portion 14 of the ceramic base member 12 are covered with the porous oxidation catalyst layers. On the oxidation catalyst layers, the combustible gas in the gas to be measured is oxidized to generate heat of reaction. In consequence, the temperature of the resistor 22 rises higher than the temperature of the gas to be measured by the reaction heat, so that a temperature difference occurs between the resistor 21 and the resistor 22. This temperature difference is proportional to the volume of the oxidized combustible gas, i.e., the volume of the combustible gas contained in the gas to be measured. For example, if the gas to be measured is an exhaust gas, there are carbon monoxide (CO), hydrocarbons (HC), a hydrogen gas ($H_2$) and the like as the components of the combustible gas.

Constant currents $I_1$ and $I_2$ are fed to the resistors 21, 22 by way of the current leads 31, 32, 41, 42, respectively. Voltages generated across the resistors 21, 22 are detected as $V_1$, $V_2$ by way of the voltage leads 33, 34, 43, 44 by the voltmeters 52, 54. The temperatures of the resistors 21, 22 can be calculated on the basis of the voltages $V_1$, $V_2$ or resistances which are quotients obtained by dividing the voltages by the currents.

FIG. 3 shows the resistance-temperature properties of the thermite comprising platinum and $Al_2O_3$. In the following measurement, the cermets were used as the resistors 21, 22.

FIG. 4 shows the measured results of temperature differences between the resistors 21, 22 when the gases to be measured having the various concentrations of hydrocarbons were allowed to flow. In the gas to be measured, there were contained a nitrogen gas ($N_2$) as a carrier gas, $C_3H_8$ and carbon monoxide as combustible gases, and an oxygen gas ($O_2$) which is necessary to burn the combustible gases. The gas to be measured was heated to 450° C.

At the time of this measurement, $Al_2O_3$ having a purity of 99.9% or more was used for the whole ceramic base member 12, and the cermet comprising platinum and $Al_2O_3$ was used for the resistors 21, 22, the current leads 31, 32, 41, 42 and the voltage leads 33, 34, 43, 44. This cermet has the resistance-temperature properties shown in FIG. 3.

Constant currents of 10 mA were applied from the constant current sources 51, 52 to the resistors 21, 22 by way of the current leads 31, 32, 41, 42, respectively. The voltages across the resistors 21, 22 were detected by way of voltage leads 33, 34, 43, 44 by the voltmeters 52, 54. On the basis of these voltages, resistance values were calculated, and temperatures were then obtained in accordance with the characteristic equation of FIG. 3.

In FIG. 4, the curve of $C_3H_8$ has a gradient larger than that of carbon monoxide, which indicates that the combustible gas sensor of the present invention is more sensitive to $C_3H_8$ than to carbon monoxide. This reason is that the heat of combustion of $C_3H_8$ is larger than the heat of combustion of carbon monoxide. In general, most of hydrocarbons (HC) contained in the exhaust gas of an automobile or the like have more than three carbon atoms, and hence the combustion heat of these hydrocarbons is larger than that of carbon monoxide or $H_2$, so that the sensitivity of the sensor to the hydrocarbons is higher.

Figure 5:
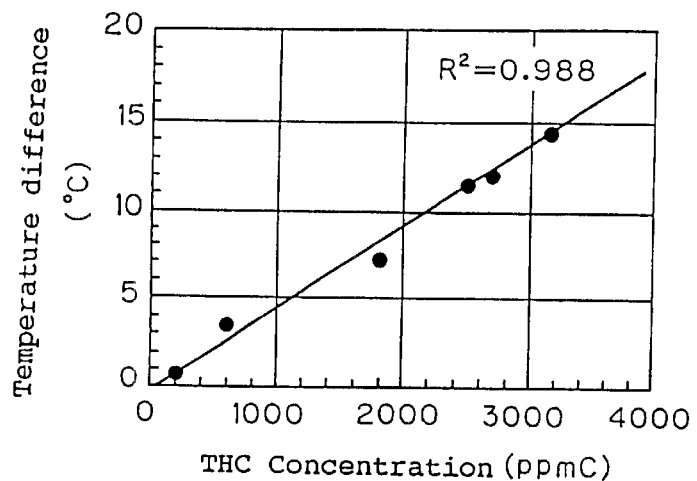
FIG. 5 is a graph showing the relation between the temperature difference between the resistors 21 and 22 and the concentration of the combustible gas in the case that an exhaust gas of an automobile is used as a gas to be measured.

FIG. 5 shows the results obtained by detecting the combustible gas in the exhaust gas of an automobile by the use of the combustible gas sensor shown in FIGS. 1 and 2. In the automobile having a 2.0 liter serial 4-cylinder engine, the combustible gas sensor 10 was arranged on the downstream side of the catalyst, and the engine of the automobile was then idled. Various catalysts having different deterioration degrees were used, and the concentration of hydrocarbons was changed to measure the temperature differences of the sensor.

In this experiment, the concentration of the hydrocarbons was measured by the use of MEXA-8420 made by Horiba Co., Ltd. (hydrocarbon measurement by a hydrogen flame ionization detection method). Since kinds of hydrocarbons (HC) contained in the exhaust gas were not definite, the hydrocarbon concentration was expressed as THC (total hydrocarbons) in terms of the number of carbon atoms. For example, if the concentration of $C_3H_8$ is 1000 ppm, the hydrocarbon concentration is expressed as 3000 ppmc obtained by multiplying 1000 ppm by the number of carbon atoms, i.e., 3. Furthermore, if the concentration of $C_3H_6$ is 1000 ppm, the hydrocarbon concentration is similarly expressed as 3000 ppmc. For discrimination from the unit of ppm which has usually been used, the unit of ppmC is used.

Figure 6:
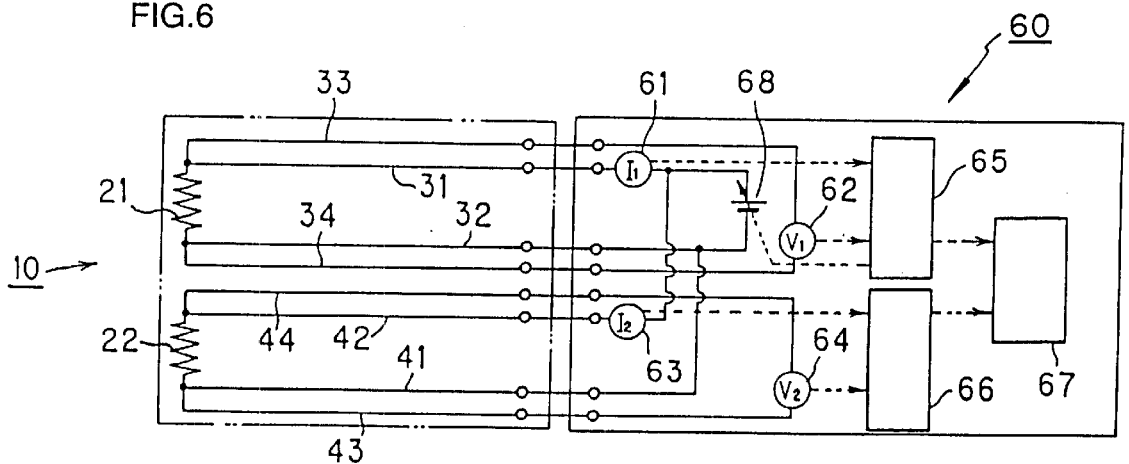
FIG. 6 shows the electric circuit diagram of the combustible gas sensor shown in FIGS. 1A to 1C and an electric circuit diagram of a feedback control device.

In the experiment of FIG. 5, the resistors 21 were self-heated to 500° C. by a feedback control device 60. To the resistors 22, there is applied a current having the same value as in the case of the resistors 21. FIG. 6 shows an electric circuit diagram of the combustible gas sensor 10 and an electric circuit diagram of the feedback control device 60.

Referring to FIG. 6, in order to heat the resistor 21 (having no oxidation catalyst layer), a voltage is applied from a variable power source 68 to the resistor 21. The current $I_1$ flowing through the resistor 21 is detected by an ammeter 61, and the voltage $V_1$ across the resistor 21 is detected by a voltmeter 62. The current $I_1$ and the voltage $V_1$ are input to an arithmetic circuit 65, and in this arithmetic circuit 65, the resistance value of the resistor 21 is obtained by dividing the voltage $V_1$ by the current $I_1$.

If this measured resistance value is lower than a resistance value corresponding to a predetermined temperature, in this case, 500° C. the higher voltage is applied from the variable power source 68 to the resistor 21. On the other hand, if this resistance value is higher than the resistance value corresponding to the predetermined temperature, the lower voltage is applied from the variable power source 68 to the resistor 21. In this way, the temperature of the resistor 21 is constantly maintained at 500° C.

The same voltage as applied to the resistor 21 is also applied from the variable power source 68 to the resistor 22. If the resistors 21, 22 have the same heat capacity and the same heat release conditions are employed, the resistors 21, 22 are heated to the same temperature. Furthermore, an ammeter 63 detects the current $I_2$ flowing through the resistor 22, and a voltmeter 64 detects the voltage $V_2$ across the resistor 22. The current $I_2$ and the voltage $V_2$ are input to an arithmetic circuit 66, which calculates the resistance value of the resistor 22.

A comparator 67 compares the resistance value of the resistor 21 output by the arithmetic circuit 65 with that of the resistor 22 output by the arithmetic circuit 66.

If the gas to be measured does not contain any combustible gas, a temperature difference and a resistance difference between the resistors 21, 22 are ideally 0,respectively.

On the other hand, if the gas to be measured contains the combustible gas, the heat of combustion is generated in accordance with the concentration of the combustible gas, so that the temperature of the resistor 22 correspondingly rises and a temperature difference occurs between the resistors 21, 22. In consequence, this temperature difference is proportional to the concentration of the combustible gas.

According to a measurement method by self-heating, the measurement can stably be accomplished, even if the temperature of the gas to be measured noticeably fluctuates as in the case of the exhaust gas of an automobile. Because of the self-heating, the follow-up properties of the temperature are excellent, and therefore the temperature can constantly be maintained, even if the temperature of the exhaust gas fluctuates abruptly.

Figure 7:
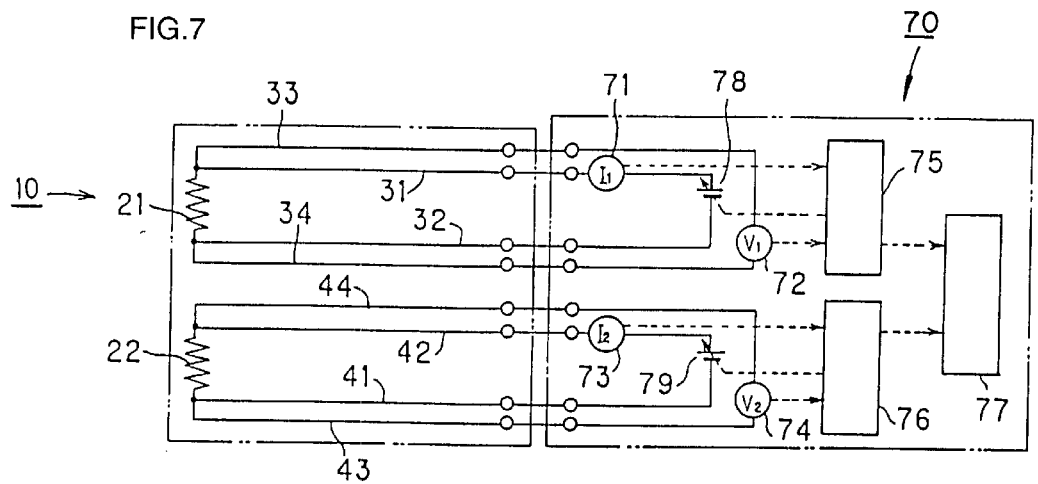
FIG. 7 shows the electric circuit diagram of the combustible gas sensor shown in FIGS. 1A to 1C and an electric circuit diagram of another feedback control device.

FIG. 7 is another electric circuit diagram for use in a method using the combustible gas sensor of the present invention or a method for measuring the concentration of the combustible gas.

In FIG. 7, the resistors 21, 22 are independently self-heated to a certain temperature, for example, 500° C. The technique of the self-heating to the certain temperature is as described above. In FIG. 6, the resistance values of the resistors 21, 22 are determined, but in FIG. 7, powers fed to the resistors 21, 22 are determined.

In order to heat the resistors 21, 22, voltages are applied from variable power sources 78, 79 to the resistors 21, 22. Ammeters 71, 73 detect the currents $I_1$, $I_2$ flowing through the resistors 21, 22, and voltmeters 72, 74 detect the voltages $V_1$, $V_2$ across the resistors 21, 22. The current $I_1$ and the voltage $V_1$ are input to an arithmetic circuit 75, and the current $I_2$ and the voltage $V_2$ are input to an arithmetic circuit 76. The arithmetic circuit 75 measures the resistance value and the power of the resistor 21, and the arithmetic circuit 76 measures the resistance value and the power of the resistor 22.

When the resistance values are lower than resistance values corresponding to a predetermined temperature, higher voltages are applied from the variable power sources 78, 79 to the resistors 21, 22. On the other hand, when the resistance values are higher than resistance values corresponding to a predetermined temperature, lower voltages are applied from the variable power sources 78, 79 to the resistors 21, 22.

A comparator 77 compares the power of the resistor 21 output by the arithmetic circuit 65 with that of the resistor 22 output by the arithmetic circuit 66.

The power on the side of the resistor 22 is reduced as much as energy generated at the combustion of the combustible gas, and a power difference represents the concentration of the combustible gas.

Figure 8:
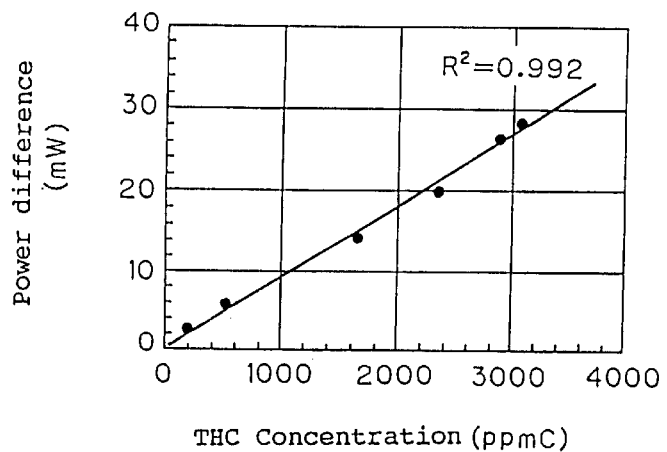
FIG. 8 is a graph showing the relation between a difference between electric powers fed to the resistors 21 and 22 and the concentration of the combustible gas.

FIG. 8 shows the relation between the concentration of hydrocarbons as the combustible gas and the power difference.

The relation was measured in the same manner as in the correlation of FIG. 6. The advantage of using the method of FIG. 7 is that both the resistors 21, 22 can be controlled to the same temperature, and so the heat transmitted from the oxidation catalyst layer 24 to the resistor 21 can be ignored, which permits the precise measurement.

Figure 9:
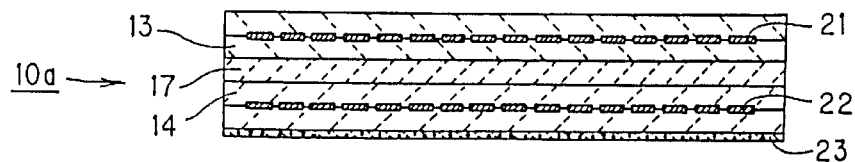
FIG. 9 is a schematic view of another embodiment of the combustible gas sensor according to the present invention.

FIG. 9 shows another embodiment of the combustible gas sensor according to the present invention. FIG. 9 corresponds to the sectional view taken along the line A–A' in FIG. 1A.

In the combustible gas sensor 10 of FIGS. 1A to 1C, the space 15 is interposed between the temperature portions of the ceramic base member 12. On the contrary, in the combustible gas sensor 10a of FIG. 9, no space is formed between the temperature sensitive portions 13, 14 of the ceramic base member 12, and the ceramic base member 17 is continuously filled into the space between the temperature sensitive portion 13 and the temperature sensitive portion 14. In addition, any oxidation catalyst layer 23 is not formed on the side of the ceramic base member 17.

When the resistors 21, 22 are controlled to a predetermined temperature to measure the power difference, any space does not have to be provided, because there is no influence of the heat transmission to the resistor 21. The constitution of no space is preferable, because it permits the miniaturization of the combustible gas sensor and the improvement of mechanical strength.

In the combustible gas sensor 10, if the resistor 21 is oriented toward the upstream side of the gas to be measured, the resistor 21 is apt to be cooled, as compared with the case that the resistor 21 is oriented toward the downstream side of the gas to be measured, so that a temperature difference occurs between the resistor 21 and the resistor 22, even if there is no combustible gas. This temperature difference is affected by the flow rate and the temperature of the gas to be measured, which is one cause of bringing about errors of the measured values.

On the other hand, in the combustible gas sensor 10a of FIG. 9, any space is not present, whereby the temperature difference does not take place any longer when there is no combustible gas, so that the combustible gas sensor is scarcely affected by the attachment direction of the combustible gas sensor to the flow of the gas to be measured and the flow rate of the gas to be measured.

Figure 10:
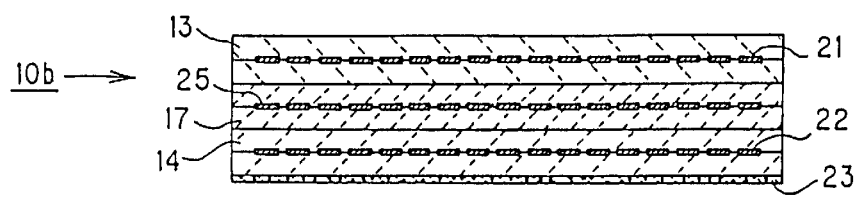
FIG. 10 is a schematic view of still another embodiment of the combustible gas sensor according to the present invention.

FIG. 10 shows another embodiment of the combustible gas sensor according to the invention. FIG. 10 corresponds to the sectional view taken along line A–A'in FIG. 1A. In the combustible gas sensor 10b of FIG. 10, any space is not interposed between the temperature sensitive portions of the ceramic base member 12, as in the case of the combustible gas sensor of FIG. 9.

In the embodiment shown in FIG. 10, heaters 25 for heating the resistor 21 are arranged between the temperature sensitive portion 13 and the temperature sensitive portion 14. A voltage or a current which is applied to the heaters 25 can be controlled so that the temperature of the resistor 21 may be a predetermined level, whereby the arithmetic operation of the resistance value or the power of the resistor 21 or 22 is advantageously unnecessary. Even when there is no combustible gas, the temperature of the resistor 21 is different from that of the resistor 22 on occasion, but this temperature difference can be compensated by the heaters 25.

In one embodiment of the electric circuit of the combustible gas sensor 10b, more leads for feeding the electric power to the heaters 25 are required, as compared with the electric circuit of FIG. 2.

Figure 11:
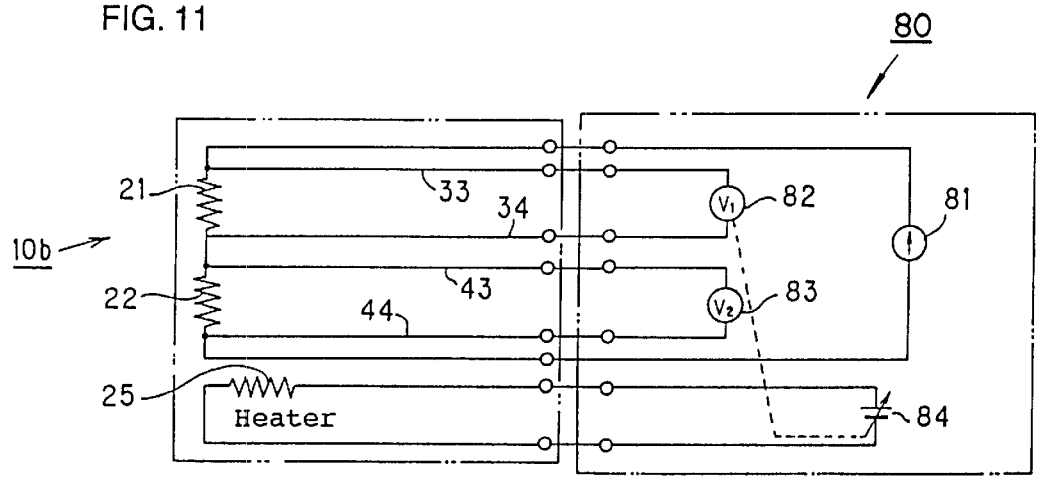
FIG. 11 shows the electric circuit diagram of the combustible gas sensor shown in FIG. 10 and an electric circuit diagram of an arithmetic device.

On the other hand, FIG. 11 shows another embodiment of the electric circuit of the combustible gas sensor 10b. The resistors 21 and 22 are connected to a constant current source 81 in series, whereby the number of the leads can be decreased.

According to the electric circuit of FIG. 11, the temperature of the resistor 21 can be constantly maintained. From a variable power source 84, an electric power is fed to a heater 86. A voltmeter 82 detects the voltage across the resistor 21, and if the resistance value across the resistor 21 is lower than a resistance value corresponding to a predetermined temperature, a larger power is fed from the variable power source 84 to the resistor 21. On the other hand, if this resistance value is higher than the resistance value corresponding to the predetermined temperature, a smaller power is fed from the variable power source 84 to the heaters 25. Incidentally, a voltmeter 83 detects the voltage across a resistor 82.

Figure 12:
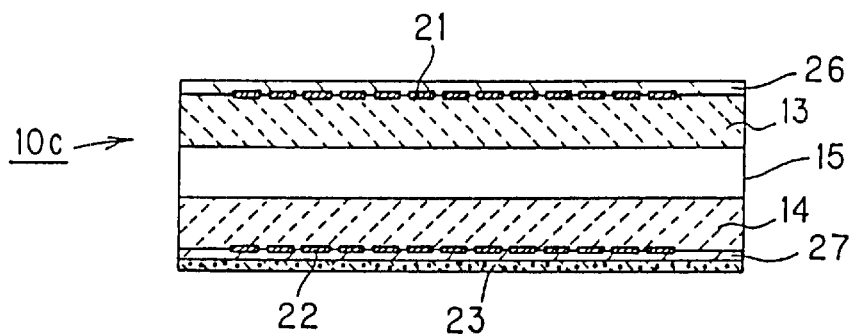
FIG. 12 is a schematic view of another embodiment of the combustible gas sensor according to the present invention.

In the embodiment shown in FIG. 12, the resistors 21 are buried in the temperature sensitive portion 13 at a position close to the surface opposite to the space 15. Similarly, the resistors 22 are buried in the temperature sensitive portion 14 at a position close to the surface opposite to the space 15.

In the combustible gas sensor 10 of FIG. 1, the resistors 21 and 22 are interposed between the ceramic sheets. On the contrary, in the combustible gas sensor 10c of FIG. 12, the resistors 21 and 22 are covered with the dense ceramic layers 26 and 27. That is to say, the resistors 21 are formed on the surface of the ceramic sheet by printing, and the resistors 21 are further formed by printing on the surface of the covering dense ceramic layer 26 with which the resistors 21 are covered. Next, the ceramic sheet, the resistors 21 and the dense ceramic layer 26 are simultaneously baked. The dense ceramic layers 26, 27 are formed on the surfaces of the temperature sensitive portions 13, 14 that are opposite to the space 15. The dense ceramic layers 26, 27 are in a dense state so as not to come in contact with the gas to be measured. The dense ceramic layer 26 covers the resistors 21 and the dense ceramic layer 27 covers the resistors 22, and the oxidation catalyst layer 23 covers the dense ceramic layer 27. The thickness of the dense ceramic layers 26, 27 is preferably in the range of about 10 and 30 μm.

Because of the formation of the thin dense ceramic layers 26, 27, the resistors 21, 22 can advantageously be placed very close to the gas to be measured. In particular, the resistors 22 are placed close to the oxidation catalyst layer 23, and therefore, heat can easily be transmitted to the resistor 22 by way of the oxidation catalyst layer 23, so that reliability and sensitivity can be improved.

Figure 13:
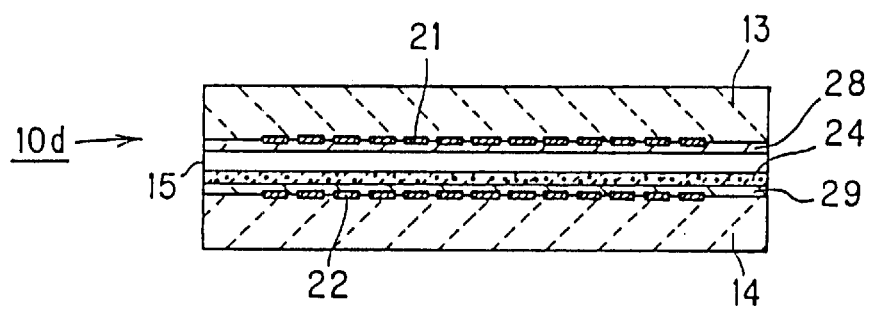
FIG. 13 is a schematic view of another embodiment of the combustible gas sensor according to the present invention.

In the embodiment shown FIG. 13, the resistors 21, 22 and the oxidation catalyst layer 24 are placed close to the space 15. In this embodiment, the dense ceramic layer 28 covers the resistors 21, and the dense ceramic layer 29 covers the resistors 22. Furthermore, the oxidation catalyst layer 24 covers the dense ceramic layer 29. The surface of the dense ceramic layer 28 and that of the oxidation catalyst layer 24 are exposed to the space 15. According to such a constitution, the temperatures of the resistors 21, 22 are close to the temperature of the gas to be measured that is flowing through the space 15. Thus, the gas to be measured can flow uniformly to the resistors 21, 22 through the space 15, so that the resistors 21, 22 are scarcely affected by the attachment direction of the combustible gas sensor and the flow rate of the gas.

Figure 14:
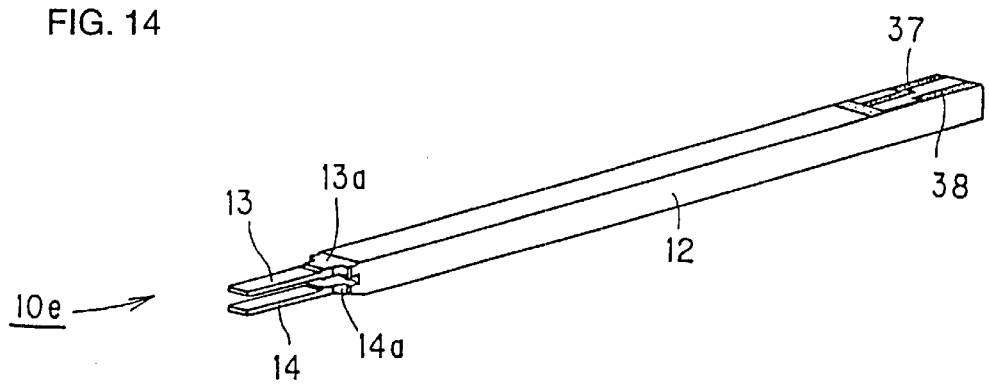
FIG. 14 is a schematic view of another embodiment of the combustible gas sensor according to the present invention.

In the embodiment shown in FIG. 14, the temperature sensitive portions 13, 14 have a plate form, and these plates are thin and have a narrow width. According to such a conformation, the heat capacity of the temperature sensitive portions 13, 14 can be decreased, and the reliability can be improved preferably. The temperature sensitive portions 13, 14 are formed integrally with the ceramic base member 12 by way of connecting portions 13a, 14a which extend gradually thinly and narrowly from the main body of the ceramic base member 12.

Next, reference will be made to a method for detecting the deterioration of a catalyst such as an automobile exhaust gas cleaning catalyst which intends to eliminate a combustible gas.

Such a catalyst can oxidize the combustible gas contained in the exhaust gas and can reduce nitrogen oxides contained in the exhaust gas. If the catalyst deteriorates, it cannot satisfactorily oxidize the combustible gas any longer, and hence the combustible gas contained in the exhaust gas increases on the downstream side of the catalyst.

Figure 15:
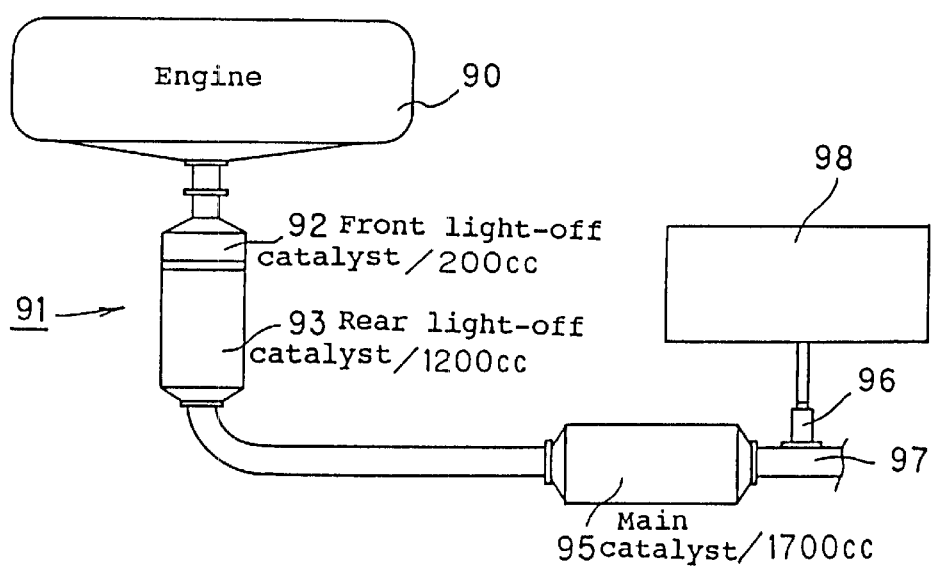
FIG. 15 is an illustrative view of the exhaust system of an automobile engine.

Thus, as shown in FIG. 15, the combustible gas sensor 10 is arranged on the downstream side of automobile exhaust gas cleaning catalysts 92, 93, 95 to detect the combustible gas contained in the exhaust gas, whereby the deterioration of the catalysts is detected.

In an exhaust system, a light-off catalyst 91 is arranged on the downstream side of a 2.0 liter serial 4-cylinder engine 90, and on its downstream side, a main three-dimensional catalyst 95 is further arranged. The light-off catalyst 91 comprises a front light-off catalyst 92 and a rear light-off catalyst 93. A casing 96 is arranged on the downstream side of the three-dimensional catalyst 95, in which the combustible gas sensor 10 is disposed. The temperature sensitive portions 13, 14 of the combustible gas sensor 10 are inserted into an exhaust pipe in order to detect the exhaust gas.

As shown in Tables 1 and 2, four different combinations A to D of catalysts are prepared so as to collect four kinds of hydrocarbon exhaust gases. Table 2 shows the results of the hydrocarbon exhaust gases in the respective combinations at the time of FTP running.

TABLE 1

| Combination of Catalysts | Front Light-off Catalyst 200 cc | Rear Light-off Catalyst 1,200 cc |
|---|---|---|
| A | New | New |
| B | Aged at 750° C. for 100 hr | Aged at 850° C. for 100 hr |
| C | Aged at 850° C. for 100 hr | Aged at 850° C. for 100 hr |
| D | No catalyst | Aged at 850° C. for 100 hr |

TABLE 2

| Combination of Catalysts | Main Catalyst 1700 cc | HC Discharge Rate (g/mile) |
|---|---|---|
| A | New | 0.043 |
| B | New | 0.048 |
| C | New | 0.058 |
| D | New | 0.074 |

With regard to the deterioration of the catalyst, the following duty is imposed on LEVs (low emission vehicles) and ULEVs (ultra low emission vehicles) in the State of California, USA. When the amount of exhausted hydrocarbons is 1.5 times as much as a regulated value of the hydrocarbons at FTP (Federal Test Procedure) running of a new car, an MIL (malfunction indicator lamp) must be turned on.

Figure 16:
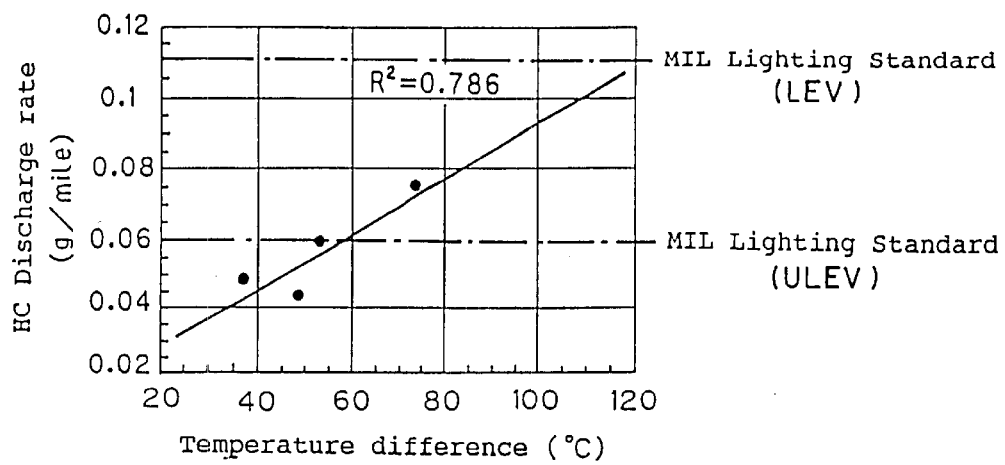
FIG. 16 is a graph showing the correlation between the discharge rate of hydrocarbons and a temperature difference between the resistors 21 and 22 after 30 seconds from the start of the engine at FTP running.

FIG. 16 is a graph showing the correlation between an output of the sensor (a temperature difference at the self-heating of the resistor 21 to 450° C.) and an amount of the exhausted hydrocarbons after 30 seconds from the start of the engine at the FTP running. It is confirmed that the correlation is present between the output of the sensor and the amount of the exhausted hydrocarbons, and therefore from the output of the sensor, the lighting of the MIL can be judged.

Figure 17:
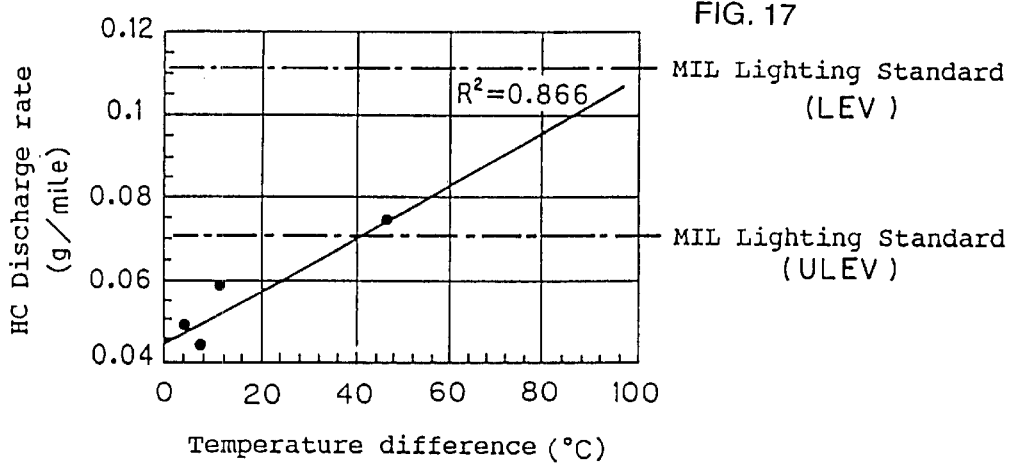
FIG. 17 is a graph showing the correlation between the discharge rate of hydrocarbons and a temperature difference between the resistors 21 and 22 after 50 seconds from the start of the engine at the FTP running.

FIG. 17 is a graph showing the relation between an output of the sensor and an amount of the exhausted hydrocarbons after 50 seconds from the start of the engine at the FTP running. Also in this case, it is confirmed that the correlation is present between the output of the sensor and the amount of the exhausted hydrocarbons, and therefore from the output of the sensor, the lighting of the MIL can be judged.

Figure 18:
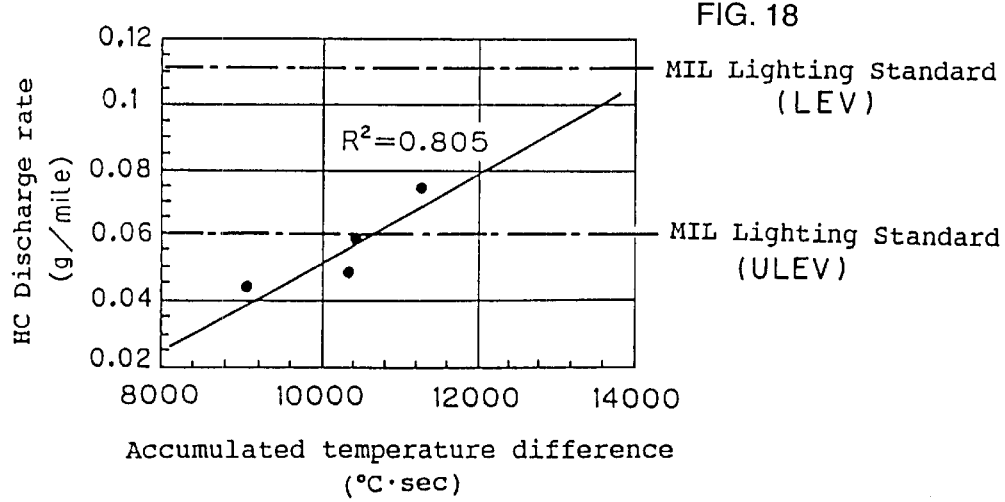
FIG. 18 is a graph showing the correlation between the discharge rate of hydrocarbons and a temperature difference between the resistors 21 and 22 which is accumulated for 500 seconds at the FTP running.

FIG. 18 is a graph showing the correlation between a value obtained by accumulating temperature differences between the resistors 21 and 22 every second for 500 seconds after the start of the engine and an amount of the exhausted hydrocarbons. Also in this case, it is confirmed that the correlation is present between the output of the sensor and the amount of the exhausted hydrocarbons, and therefore from the output of the sensor, the lighting of the MIL can be judged.

Figure 19:
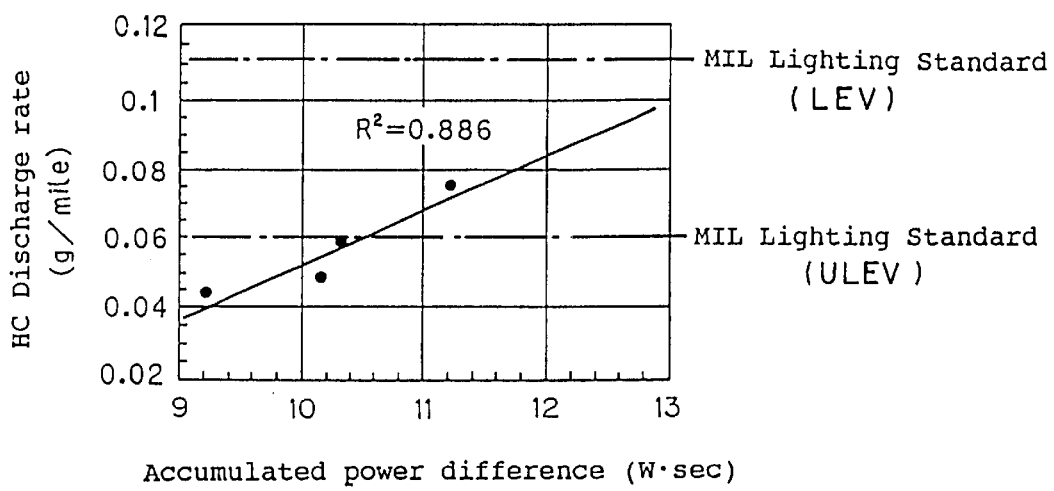
FIG. 19 is a graph showing the correlation between the discharge rate of hydrocarbons and a difference between electric powers fed to the resistors 21 and 22 which is accumulated for 500 seconds at the FTP running.

FIG. 19 is a graph showing the correlation between a value obtained by accumulating power differences between the resistors 21 and 22 every second at the time of the self-heating of the resistors 21, 22 at 500° C. and an amount of the exhausted hydrocarbons. Also in this case, it is confirmed that the correlation is present between the output of the sensor and the amount of the exhausted hydrocarbons, and therefore from the output of the sensor, the lighting of the MIL can be judged.

Preferable Embodiments and Modified Embodiments

The ceramic base member is preferably made of an electrically insulating oxide ceramic material such as $Al_2O_3$. The purity of $Al_2O_3$ is preferably 99% or more, more preferably 99.9% or more. The employment of the high-purity $Al_2O_3$ intends to prevent that impurities reacts with the resistors, so that the resistance values and the resistance temperature characteristics of the resistors change.

In particular, the content of $SiO_2$ is preferably minimized. The sintering property of the ceramic material can be improved by adding $Y_2O_3$ or $ZrO_2$, which can previously be added, because it does not react with a noble metal that can be used as the resistors.

In the case that a conductive ceramic base member such as $ZrO_2$ is used, the resistors may be wrapped in an insulating ceramic material such as $Al_2O_3$.

The temperature at which the green sheet, the resistors, the leads and the like printed on its surface are baked is preferably 1500° C. or more, because there can be minimized the change of a resistance which is caused by the re-sintering of the metal contained in the resistors, when the combustible gas sensor is used at a high temperature.

Preferably, the resistors are made of a cermet comprising the same ceramic material as the ceramic base member and a noble metal having a positive resistance temperature coefficient such as Pt, Rh or Pd or its alloy. The adhesion of the resistors and the ceramic base member can be heightened by the use of the same ceramic material as the ceramic base member.

A low-melting noble metal such as Au or Ag, Ni or the like having a positive resistance temperature coefficient is preferably added to the resistors, because the cermet resistors are apt to be sintered at the time of the baking of the ceramic base member, and the change of the resistance values during use at a high temperature can be minimized.

In the combustible gas sensor or the sensor element according to the present invention, the resistors, the leads and the terminal pads are preferably printed on the ceramic base member. However, blade coating, spray coating or the like is also acceptable.

The oxidation catalyst layer is preferably made by supporting an oxidation catalyst on the same porous material as the ceramic base member. That is to say, preferably, a metal which functions as the oxidation catalyst or a cermet of the metal and a ceramic material is printed and simultaneously baked to obtain a porous material, and an oxidation catalyst such as Pt, Pd or Rh is further supported on the cermet. The metal for the oxidation catalyst contained in the cermet oxidizes and coarsens in the process of the simultaneous baking, and therefore the initial performance of the oxidation catalyst is limited. However, the performance of the oxidation catalyst can be compensated by further supporting the catalyst in the state of the metal particles. After long-term use, the supported catalyst spatters, so that the performance of the oxidation catalyst deteriorates. On the other hand, the oxidation catalyst metal contained in the cermet is exposed to the exhaust gas, and in consequence, the oxidation catalyst metal becomes fine particles, so that the performance of the oxidation catalyst is improved to compensate the deterioration of the oxidation catalytic activity of the supported catalyst.

Figure 20:
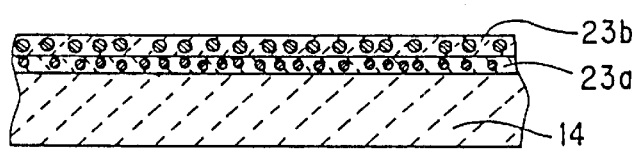
FIG. 20 is an enlarged view of a portion represented by B in FIG. 1C.

In FIG. 20, the oxidation catalyst layer 23 has a double layer structure, which is different from the embodiment of FIG. 1. The oxidation catalyst layer 23 comprises a cermet layer 23a which covers the surface of the ceramic base member 14 and a catalyst supporting layer 23b which covers the surface of the cermet layer 23a. Both the cermet layer 23a and the catalyst supporting layer 23b contain the oxidation catalyst and are porous. After the formation of the cermet layer 23a, a porous ceramic layer, for example, a layer comprising $Al_2O_3$ is formed so as to support the catalyst all over this layer. Such a constitution is advantageous, because a large amount of the oxidation catalyst can be supported. As the oxidation catalyst, not only Pt but also Pd and Rh can be used.

The oxidation catalyst layers 23, 24 are preferably covered with another porous catalyst layer supporting a catalyst capable of oxidizing carbon monoxide. In this case, the same catalyst layer is also formed on the surface of the temperature sensitive portion 13 of the resistors 21. This constitution is preferable, because the influence across carbon monoxide contained in the gas to be measured can be removed, and combustible gases such as hydrocarbons and a hydrogen gas can be more selectively detected. One example of the catalyst capable of oxidizing carbon monoxide is Au.

For the improvement of follow-up properties to temperature change, the heat capacity of the temperature sensor section is preferably designed as small as possible, so far as mechanical strength and thermal strength are allowed.

Irrespective of self heating or nearby heating, the heating is preferably such as to heat at least the resistors 21 to a certain temperature, but for example, temperature difference measurement or power difference measurement may be carried out by applying a constant voltage. In the case of the power difference measurement, the resistors 21 and the resistors 22 are preferably regulated to the same temperature, but they may be controlled to different temperatures.

When the temperature of the exhaust gas rises above a heating control temperature, the measurement may be stopped, but the temperature difference may be measured by applying a constant current, or there may be applied an electric power necessary to regulate the temperature of the resistors 21 to that of the resistors 22.

In order to detect the deterioration of the catalyst which intends to eliminate the combustible gas, it is preferable to obtain an accumulated value of the temperature differences or the power differences between the resistors. It is more preferable that the temperature difference or the power difference (which represents the concentration of the combustible gas) is multiplied by the flow rate of the gas to be measured to obtain a weight value. The flow rate of the gas to be measured, for example, the exhaust gas of an automobile may be determined by suitably selecting and then calculating one or a combination of data such as the rotational frequency of an engine, an air intake rate, a temperature, an air sucking negative pressure and a fuel filling efficiency. More preferably, the flow rate of the exhaust gas may be used in combination with the speed or the mileage of the automobile to obtain a (weight/distance) value.

In the combustible gas sensor of the present invention, every temperature sensor section is preferably provided with a potentiometric resistor. The potentiometric resistor is connected in parallel with the resistors, and for example, they are connected to the resistors by way of voltage leads. The potentiometric resistor preferably has a small resistance temperature coefficient in contrast to the resistors. A serial resistor also preferably has a small resistance temperature coefficient in contrast to the resistors. Examples of the potentiometric resistor include a ceramic base member on which a metal or a metal oxide is printed, a glass in which the particles of a metal or a metal oxide are dispersed, and a thin film and a fine wire comprising a metal or a metal oxide. An example of the metal oxide is ruthenium oxide.

The potentiometric resistor preferably covers at least a part of the surface of the ceramic base member, so that the potentiometric resistor can be trimmed by laser or the like to regulate the output voltage from the resistors at the time of the application of a current. That is to say, the potentiometric resistor can be trimmed with the laser, while a counter electromotive force generated by the application of a predetermined current to the resistors at a predetermined temperature (e.g., 25° C.) is detected as the output voltage, whereby the resistance value of the potentiometric resistor can be regulated so that the output voltage may be constant. Therefore, the value of $R_0$ can be held to a substantially constant level.

Furthermore, since the potentiometric resistor can be arranged at a position which does not come in contact with an atmosphere where the temperature is measured, and hence the potentiometric resistor scarcely deteriorates, so that the resistance value of the potentiometric resistor scarcely changes with time.

In FIGS. 21A and 21C, the potentiometric resistors 102a, 102b are preferably arranged at opposite positions at the end of the ceramic base member 12 having the temperature sensitive portions 13, 14. Since the potentiometric resistors 102a, 102b are separated from the temperature sensitive portions 13, 14, the transmission of heat from the temperature sensitive portions 13, 14 or the oxidation catalyst layers 23, 24 can be reduced.

It is preferred that the potentiometric resistor 102a is located on the side of the resistors 21, whereas the potentiometric resistor 102b is located on the side of the resistors 22. The potentiometric resistor 102a is connected to the resistors 21 by way of the voltage leads 33, 34, whereas the potentiometric resistor 102b is, connected to the resistors 22 by way of the voltage leads 43, 44. These connecting operations are easy, when the potentiometric resistors 102a, 102b and the resistors 21, 22 lie in the above-mentioned positional relation.

The potentiometric resistors 102a, 102b are preferably covered with glass layers 104a, 104b in order to improve durability. The potentiometric resistors 102a, 102b are located at positions where they are scarcely affected by high temperature, and therefore the glass covering layers of the potentiometric resistors can maintain a sufficient durability, even when the combustible gas sensor is exposed to a high temperature.

The covering of the glass on the potentiometric resistor can be accomplished by forming a slurry of a glass powder such as lead borosilicate glass, allowing this slurry to adhere onto the surface of the potentiometric resistor by immersion, blade coating or spray coating, drying the slurry which adheres onto the surface, and then baking it.

Figure 21:
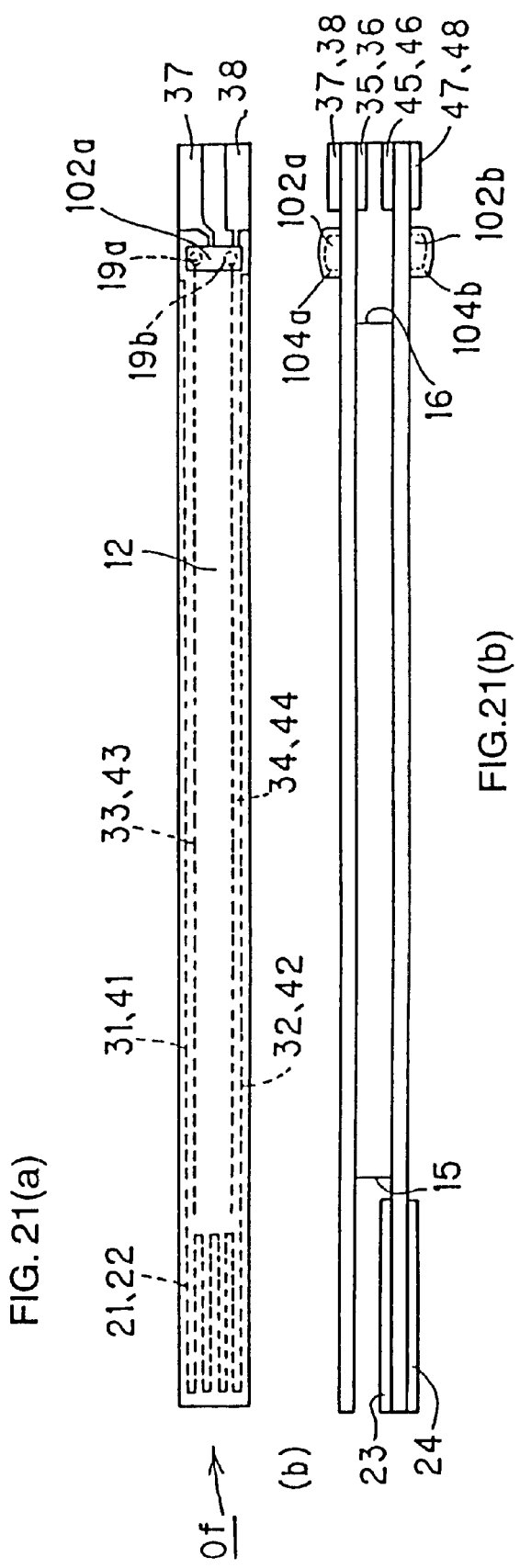
FIG. 21A is a front view of one embodiment of the combustible gas sensor according to the present invention.
FIG. 21B is a side view of one embodiment of the combustible gas sensor according to the present invention.
Figure 22:
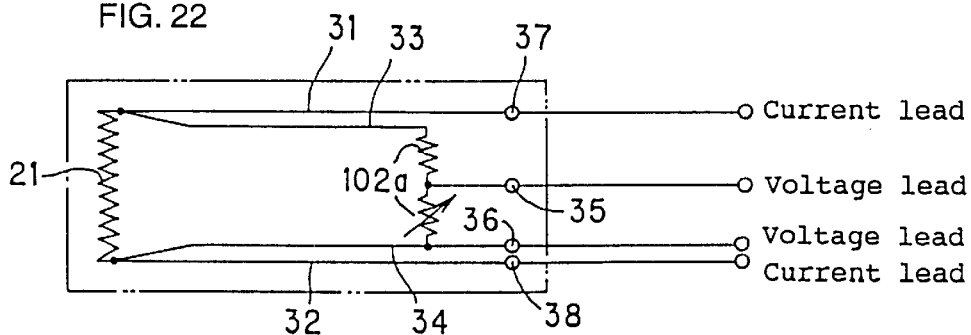
FIG. 22 is an electric circuit diagram of a part of the combustible gas sensor shown in FIGS. 21A and 21B.

FIG. 22 shows an electric circuit diagram of one temperature sensor section of the combustible gas sensor in FIGS. 21A, 21B. An electric circuit diagram of the other temperature sensor section is the same as in FIG. 22. The potentiometric resistor 102a is connected in parallel with the resistors 21 by way of the voltage leads 33, 34. A part of the voltage of the potentiometric resistor 102a is output from the voltage terminals 35, 36.

In another embodiment of the combustible gas sensor, the potentiometric resistors 102a, 102b in FIG. 21 are replaced by a pair of serial resistors 106a, 106b. The serial resistors 106a, 106b are covered with the glass layers 104a, 104b, as in the case of the potentiometric resistors 102a, 102b.

The leads and side passages are formed so that the resistors 21 and the serial resistor 106a may be connected in series by way of the voltage lead 34. For example, one voltage lead 34 is connected to one voltage terminal 45 by way of the serial resistor 106a, and the other voltage lead 35 is connected to the other voltage terminal 46 without being connected to the serial resistor 106a.

Figure 23:
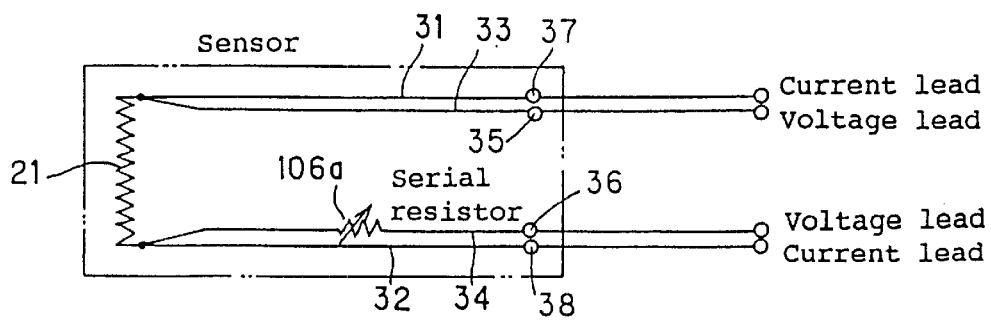
FIG. 23 is an electric circuit diagram of a part of the combustible gas sensor according to the present invention.

FIG. 23 is an electric circuit diagram of one temperature sensor section in the case that the serial resistor is disposed. The functions of both the temperature sensor sections are identical, and therefore the function of one temperature sensor section will be described, and the description of the other temperature sensor section will be omitted.

In FIG. 23, the resistor 21 is connected in series with the serial resistor 106a by way of the voltage lead 34. According to the second aspect of the invention, the serial resistor 106a is trimmed by laser irradiation in accordance with the resistance value of the resistor 21. For example, if the resistance value of the resistor 21 is 10Ω, the serial resistor is regulated to 10 kΩ. If the resistance value of the resistor 21 is 20Ω, the serial resistor is regulated to 20 kΩ.

As a technique of the regulation, in the first place, a constant current is allowed to flow through the resistor 21 by way of the current leads 31, 32, and the voltage of the resistor 21 is detected by way of the voltage leads 33, 34 and the resistance of the resistor 21 is then calculated. For example, $R_0$ of the resistor 21 can be measured. Here, since no current substantially flows through the voltage leads, the voltage applied to the serial resistor 106a is negligible.

Next, the resistance value of the serial resistor 106a is regulated by trimming. An ohmmeter is connected to the voltage terminals 35, 36, and the total resistance of the resistor 21, the serial resistor 106a and the voltage leads 33, 34 is then detected. Afterward, the resistance value of the serial resistor 106a is regulated by trimming so that this total resistance may have a certain relation with the resistance of the resistor 21. Typically, this total resistance is regulated so as to be proportional to the resistance of the resistor 21.

In inputting the information of the sensor element into another electric circuit, a central arithmetic unit or an interface, the electric circuit is connected to the voltage terminals 35, 36, and the total resistance of the resistor 21, the serial resistor 106a and the voltage leads 33, 34 is then detected. Afterward, the resistance of the resistor is calculated backward on the basis of the total resistance in accordance with the above-mentioned certain relationship.

When a temperature is measured by the use of the sensor element, a current is applied through the current terminals 36, 37 and the resistance of the resistor 21 is then detected from the voltage terminals 35, 36.

It is preferred that the resistance of the serial resistor is significantly larger than that of the resistor, and the resistance of the serial resistor is preferably 100 times or more, more preferably 500 times or more, most preferably 1000 times or more as much as that of the resistor. According to this constitution, the above-mentioned combined resistance can be protected from the influence of a resistance change by the temperature change of the resistor.

In the case that temperature control is made in a self heating state, a voltage and a current value change in accordance with the resistance value of the resistor, and therefore it is necessary to calculate the resistance on the basis of the current and the voltage. However, it is not necessary to input the information of $R_0$ of each sensor to the computer or the interface of an automobile. In this case, it is preferred that powers required to heat the resistors 21, 22 to a predetermined temperature are set so that these powers may be as equal as possible to each other. According to such a constitution, when the resistors 21, 22 are heated to the same temperature, the calculated resistances are equal to each other.

For instance, if the resistor 21 having a resistance value of 10Ω and the resistor 22 having a resistance value of 20Ω is combined, the potentiometric resistance of the resistor 21 can be regulated with 1/1, and the potentiometric resistance of the resistor 22 can be regulated with 1/2, so that output voltages thereof are equal to each other.

When the resistor 21 is heated to 500° C. its resistance value is double, i.e., 20Ω, and if a current value at this time is 0.2 A, an output voltage is 20×0.2=4 V. Under the conditions, a power applied to the resistor 21 is 0.2×0.2×20=0.8 W.

On the other hand, the current flowing through the resistor 22 is smaller than the current of the resistor 21 as much as an increment of the resistance value, but if the power required to heat the resistor 22 to 500° C. is equal to the power required to heat the resistor 21, the current is $(0.8/40)^{1/2}$, because the resistance of the resistor 22 at 500° C. increases from 20Ω to 40Ω. Then, the output voltage of the resistor 22 is $(0.8/40)^{1/2} \times 40 = (0.8 \times 40)^{1/2}$. Since regulated to 1/2 with the potentiometric resistance, the output voltage is its 1/2, i.e., $(0.8 \times 40)^{1/2}/2$. The operational resistance is operational resistance of the resistor 21, i.e., 20Ω. This means that the powers necessary to heat up to the same temperature are equal to each other.

This requirement can be met by forming the elements having all the same shape (size). That is to say, the resistors are printed on ceramic sheets, and these ceramic sheets are laminated, cut, and then baked to form many sheets. Next, the resistors 21, 22 are combined in the sheets, whereby the thickness of the ceramic sheets can be uniformed and the heat capacity of the resistors 21 and 22 can also be uniformed.

A combustible gas sensor according to the invention is excellent in durability at a high temperature, and it can measure a gas to be measured whose temperature largely changes.

According to a method for measuring the concentration of a combustible gas of the present invention, the concentration of the combustible gas can be measured even at a high temperature and even when the temperature of the gas to be measured largely changes.

According to a method for detecting the deterioration of a catalyst, the concentration of the combustible gas can be measured even when the temperature of the gas to be measured largely fluctuates.

What is claimed is:

1. A method for detecting the deterioration of a treatment catalyst which oxidizes a combustible gas in a gas to be treated, the method consisting essentially of:

(1) providing a combustible gas sensor which consists essentially of a base member having a first temperature sensor section and a second temperature sensor section, wherein the first temperature sensor section includes a first temperature sensitive portion of a dense ceramic material and the second temperature sensor section includes a second temperature sensitive portion of a dense ceramic material;

a first resistor buried in the first temperature sensitive portion and having a positive resistance temperature coefficient;

a first pair of current leads for providing current to the first resistor;

a first pair of voltage leads for detecting a voltage across the first resistor;

a second resistor buried in the second temperature sensitive portion and having a positive resistance temperature coefficient;

a second pair of current leads for providing current to the second resistor;

a second pair of voltage leads for detecting a voltage across the second resistor; and a porous oxidation catalyst layer which covers at least a part of a surface of the second temperature sensitive portion in which said second resistor is buried to catalyze oxidation of a combustible gas;

(2) passing the gas to be treated through the treatment catalyst to obtain a treated gas;

(3) contacting the treated gas with said sensor;

(4) applying a current I1 to the first resistor to determine a voltage V1 of the first resistor;

(5) applying a current I2 to the second resistor to determine a voltage V2 of the second resistor;

(6) determining a difference between temperatures of the first resistor and the second resistor or a difference between electric power fed to the first resistor and the second resistor on the basis of the current I1, the current I2, the voltage V1 and the voltage V2;

(7) determining the concentration of the combustible gas in the treated gas based on said temperature difference or said electric power difference; and (8) comparing the concentration of the combustible gas determined in (7) with a predetermined value of concentration representative of deterioration of said treatment catalyst.

2. The method for detecting the deterioration of a catalyst according to claim 1 wherein output signals of the combustible gas sensor are accumulated for a predetermined period of time.

3. The method for detecting the deterioration of a catalyst according to claim 1 wherein a product of the output signal of the combustible gas sensor and the flow rate of the gas to be measured is calculated.

4. The method for detecting the deterioration of a catalyst according to claim 3 wherein the products are accumulated for a predetermined period of time.

* * * * *